United States Patent [19]

Goertz et al.

[11] Patent Number: 4,478,976
[45] Date of Patent: Oct. 23, 1984

[54] WATER-INSOLUBLE PROTEIN MATERIAL, ITS PREPARATION AND ITS USE

[75] Inventors: Hans-Helmut Goertz; Stefan Marcinowski, both of Ludwigshafen; Axel Sanner, Frankenthal, all of Fed. Rep. of Germany

[73] Assignee: BASF Aktiengesellschaft, Fed. Rep. of Germany

[21] Appl. No.: 420,317

[22] Filed: Sep. 20, 1982

[30] Foreign Application Priority Data

Sep. 25, 1981 [DE] Fed. Rep. of Germany ....... 3138194

[51] Int. Cl.³ .............................................. C08J 9/00
[52] U.S. Cl. .................................... 525/54.1; 527/200; 527/201; 527/207; 435/174; 435/177; 435/180; 427/2; 427/414
[58] Field of Search ............... 525/54.1; 527/200, 201, 527/207; 435/174, 177, 180; 427/2, 414

[56] References Cited

U.S. PATENT DOCUMENTS 3,759,849  9/1973  Yamamoto et al. ................ 527/201
4,246,351  1/1981  Miyake et al. ...................... 435/180
4,371,612  2/1983  Matsumoto et al. ................ 435/177

FOREIGN PATENT DOCUMENTS 582373  9/1959  Canada .............................. 527/201

OTHER PUBLICATIONS

Dechema Monographien, vol. 84, Verlag Chemie (1979), pp. 145–169.
Enzymologia 31, (1966), pp. 214–224.
Biotechnol. & Bioeng. 9 (1967) pp. 603–615.

*Primary Examiner*—John Kight
*Assistant Examiner*—Nathan M. Nutter
*Attorney, Agent, or Firm*—Keil & Weinkauf

[57] ABSTRACT

A biologically active protein which is bonded to a water-insoluble porous copolymer based on N-vinylimidazole and/or substituted N-vinylimidazoles and monomers which can be copolymerized therewith, its preparation and its use for carrying out enzymatic reactions.

5 Claims, No Drawings

WATER-INSOLUBLE PROTEIN MATERIAL, ITS PREPARATION AND ITS USE

The present invention relates to a water-insoluble protein material, its preparation, and the use of this material for carrying out enzymatic reactions.

Carriers or bonding or immobilizing enzymes have been disclosed in Dechema Monographie Volume 84, Verlag Chemie (1979), page 145 et seq.; "Immobilized Enzymes" John Wiley & Sons, New York, 1978. In practice, carriers based on biopolymers or modified biopolymers, eg. DEAE-cellulose or DEAE-Sepharose have hitherto been used for the adsorption of enzymes (Enzymologia 31 (1969), 214; and Biotechnol. Bioeng. 9 (1967), 603). However, these carriers are not very mechanically stable, have poor hydrodynamic properties and are very expensive and complicated to prepare. Finally, they are readily attacked and modified by microorganisms.

It is an object of the present invention to provide a combination of a polymer and an active protein which substantially avoids the above disadvantages.

We have found that this object is achieved by a water-insoluble, swellable protein material consisting of a biologically active protein on a water-insoluble carrier, wherein the protein is bonded to a water-insoluble, water-swellable copolymer based on N-vinylimidazole and/or substituted N-vinylimidazoles and monomers which can be copolymerized therewith.

The copolymer, which serves as a carrier for the protein material, contains not less than 10, preferably not less than 30, % by weight of N-vinylimidazole or substituted N-vinylimidazoles. Particularly suitable N-vinylimidazoles include 2-methyl-, 4-methyl-, 2-ethyl-, 2-propyl-, 2-isopropyl- and 2-phenyl-1-vinylimidazole.

The insolubility of the polymer in water is achieved, in particular, by addition of from 1 to 70, preferably from 3 to 20, % by weight of polyolefinically unsaturated monomers which can be copolymerized with the vinyl groups of the N-vinylimidazole or of the appropriate derivative. Particularly suitable monomers are benzene derivatives containing 2 or more vinyl groups, preferably divinylbenzene, polyfunctional esters of acrylic acid or methacrylic acid, such as butanediol diacrylate, polyunsaturated urea derivatives, such as divinylethyleneurea or divinylpropyleneurea, and bisacrylamides, such as methylenebisacrylamide or ethylenebisacrylamide.

It is also possible for the carrier to contain, as copolymerized units, not more than 89% by weight of other monomers which can be copolymerized with the N-vinylimidazole and divinylbenzene. Under certain circumstances, these monomers can, even without crosslinking, provide a water-insolubility which is sufficient for practical purposes (only insolubility in water is important, not insolubility in other solvents). Examples of such monomers are styrene, ($C_{1-4}$-alkyl)-styrenes, acrylic acid and methacrylic acid and alkyl esters thereof, in particular hydrophilic esters, such as hydroxyalkyl or aminoalkyl esters, and other vinylheterocyclic compounds, such as N-vinylpyrrolidone and vinylpyridine. However, the addition of more than 20% of a comonomer in most cases impairs the adsorption properties. Even the replacement of divinylbenzene by other crosslinking agents, eg. butanediol diacrylate, divinylethyleneurea or methylenebisacrylamide, may lead to less good results.

Carriers of the type mentioned which are suitable for adsorbing proteins can be obtained by free radical polymerization. For example, a mixture of the monomers can be polymerized at elevated temperature with the aid of a suitable free radical initiator, eg. an azo compound or a peroxide, where relevant with the addition of a nonpolymerization additive which causes pore formation. Such a polymerization is disclosed in, for example, German Laid-Open Application DOS No. 2,506,085. If the polymerization is carried out in a solvent, in which case water is particularly suitable for the vinylimidazoles when a water-soluble initiator is simultaneously used, the polymer is obtained as a gel (U.S. Pat. No. 2,878,183). Polymerization in solution where only the monomer and not the polymer is soluble in the solvent (precipitation polymerization) is also possible. Bead or suspension polymerization is particularly suitable, since the polymer is obtained in bead form, which is especially suitable for its use. The monomer mixture is emulsified in water, preferably together with an organic additive and using a suitable assistant, for example a high molecular weight polyvinylpyrrolidone, and is polymerized with the aid of a free radical initiator dissolved in the monomer mixture. Because the vinylimidazoles are partly water-soluble, it is advisable to add a salt to the aqueous phase (German Published Application DAS No. 1,929,501). The reverse suspension process in which the aqueous monomer phase is suspended in an inert continuous phase, for example a hydrocarbon, can also be successfully used (German Laid-Open Application DOS No. 2,324,204).

Examples A–H illustrate the preparation of suitable polymers.

EXAMPLE A

A mixture of 200 parts of 2-methyl-1-vinylimidazole, 100 parts of technical grade divinylbenzene (consisting of 50% of divinylbenzene and 50% of ethylvinylbenzene) and 300 parts of butyl acetate, in which 12 parts of lauroyl peroxide are dissolved, is dispersed in a solution of 500 parts of $Na_2SO_4.10H_2O$ in 2,500 parts of water containing 3 parts of polyvinylpyrrolidone (molecular weight=$10^6$), and the dispersion is heated at 80° C. for 8 hours, while stirring. The bead polymer is filtered off, washed with water and acetone and dried under reduced pressure.

EXAMPLE B

A mixture of 100 parts of N-vinylimidazole, 50 parts of technical grade divinylbenzene and 150 parts of ethyl acetate, in which 6 parts of azodiisobutyronitrile are dissolved, is dispersed in a solution of 250 parts of $Na_2SO_4.10H_2O$ in 1,500 parts of water containing 3 parts of polyvinylpyrrolidone (molecular weight=$10^6$), and polymerization is carried out as in Example A.

EXAMPLE C

A mixture of 50 parts of N-vinylimidazole, 31 parts of technical grade divinylbenzene and 75 parts of ethyl acetate, which contains 3 parts of azodiisobutyronitrile, is dispersed in 1,500 parts of water, in which 125 parts of $Na_2SO_4.10H_2O$ and 2 parts of polyvinylpyrrolidone (molecular weight=$10^6$) are dissolved, and polymerization is carried out as in Example A.

EXAMPLE D

A mixture of 100 parts of 2-methyl-1-vinylimidazole, 100 parts of N-vinylpyrrolidone, 100 parts of technical grade divinylbenzene and 400 parts of toluene, which contains 10 parts of benzoyl peroxide, is dispersed in a solution of 500 parts of sodium chloride and 3 parts of polyvinylpyrrolidone (molecular weight=$10^6$) in 2,500 parts of water, and polymerization is carried out as in Example A.

EXAMPLE E

A mixture of 45 parts of 2-methyl-1-vinylimidazole, 45 parts of 2-hydroxyethylmethacrylate, 10 parts of technical grade divinylbenzene and 100 parts of n-octane, which contains 4 parts of benzoyl peroxide, is dispersed in a solution of 200 parts of sodium chloride and 1 part of polyvinylpyrrolidone (molecular weight=$10^6$) in 750 parts of water, and polymerization is carried out as in Example A.

EXAMPLE F

A mixture of 90 parts of 2-methyl-1-vinylimidazole, 10 parts of N,N'-divinylethyleneurea and 100 parts of ethyl acetate, which contains 4 parts of lauroyl peroxide, is dispersed in a solution of 1 part of xanthane and 200 parts of sodium chloride in 750 parts of water, and polymerization is carried out as in Example A.

EXAMPLE G

A solution of 40 parts of N-vinylimidazole, 20 parts of methylenebisacrylamide and 5 parts of potassium peroxodisulfate in 40 parts of water is heated at 70° C. for 7 hours under nitrogen. The resulting gel is comminuted, washed with acetone and dried under reduced pressure.

EXAMPLE H

A mixture of 100 parts of N-vinylimidazole, 50 parts of technical grade divinylbenzene and 150 parts of ethyl acetate, which contains 1 part of azodiisobutyronitrile, is heated at 70° C. for 3 hours under nitrogen. The resulting polymer is comminuted, washed with acetone and dried in vacuo.

The polymers can have swelling capacities in water of from about 2 to more than 25 ml of moist volume per gram of dry substance. The adsorption of protein is generally higher with polymers which swell better than with comparable polymers which swell less, but there is no direct relationship between protein adsorption and swelling capacity.

The protein adsorption capacity of vinylimidazole-containing polymers varies according to their composition and crosslinking density, and also varies from protein to protein. Depending on the protein, addition of an inert organic solvent in which the monomers are soluble and the polymers are insoluble, eg. naphtha, octane, toluene, ethyl acetate or butyl acetate, to the polymerization mixture during preparation of the polymers may improve the adsorption capacity. Suitable additives of this type can easily be determined in random experiments. In advantageous cases, adsorption values of more than 5 g of bonded protein per g of dry polymer are achieved.

Charging of the polymeric adsorbents with protein or removal of a protein from a solution can be carried out either batchwise, by stirring the polymer into the protein solution, or continuously, by passing the protein solution over the polymer, for example in a column. If the adsorbed protein is an enzyme, this generally retains at least some of its original activity when in the adsorbed state, and can thus be used as a heterogeneous catalyst for carrying out the appropriate enzyme reaction. For example, after adsorption onto a vinylimidazole-containing polymer, the enzyme invertase has a residual activity of about 20%. Crosslinking of the adsorbed enzyme on the carrier is advantageous, in order to increase its stability. Glutardialdehyde is an example of a suitable crosslinking reagent.

For the purposes of the invention, biologically active proteins are chiefly enzymes.

Preferred enzymes which can be adsorbed onto a vinylimidazole-containing polymer are invertase, glucoseisomerase, amyloglucosidase, α- and β-amylase, aminoacid acylase, penicillinacylase and hydantoinase. Other suitable enzymes include oxidoreductases, eg. alcohol dehydrogenase, lactate dehydrogenase, aminoacid oxidase, peroxidase, catalase, glucose oxidase, alcohol oxidase, succinate dehydrogenase, glutamate dehydrogenase, uricase, phenol oxidase, catechol oxidase, monoaminooxidase, lipoxygenase, luciferase, nitrate reductase, nitrite reductase, chloroperoxidase, acetaldehyde dehydrogenase, aldehyde oxygenase, diaphorase, cholesterol oxidase, glutarthioreductase, hydroxysteroid dehydrogenase, xanthine oxidase, dopamine hydroxylase, cytochrome oxidase, diacetylreductase, superoxide dismutase and limonate dehydrogenase; transferases, eg. polynucleotide phosphorylase, dextransucrase, phosphorylase, carbamate kinase, aminotransferase, transaldolase, methyltransferase, pyruvate kinase, carbamoyl transferase, phosphofructokinase and dextran synthetase; hydrolases, eg. lipase, esterase, lactase, lysozyme, cellulase, urease, trypsin, chymotrypsin, glutaminase, asparaginase, papain, ficin, pepsin, leucine aminopeptidase, carboxypeptidase A+B, naringinase, bromelain, subtilisin, phospholipase, isoamylase, cephalosporinamidase, adenosine deaminase, penicillinase, maltase, dextranase, deoxyribonuclease, sulfatase, pullulanase, phosphatase, α-galactosidase and β-glucanase; lyases, such as tryptophanase, tyrosine decarboxylase, oxynitrilase, phenylalanine decarboxylase, phenylalanine ammoniumlase, aminoacid decarboxylase, pyruvate decarboxylase, fumarase, enolase, aspartase, aminolevulin dehydratase and carboanhydratase; isomerases, eg. aminoacid racemase and triosephosphate isomerase; and ligases, eg. glutathione synthetase.

The products according to the invention have a particularly high protein content, good hydrodynamic properties and a high mechanical stability. They are also simple to prepare.

The Examples illustrate the preparation of the protein material:

EXAMPLE 1

100 mg of a polymer prepared according to Example A (particle size from 250 to 500 μm) are stirred in 100 ml of a 0.01% strength aqueous hemoglobin solution, and the decrease in the hemoglobin content of the solution is monitored photometrically. After 20 minutes, 15% of the protein has been adsorbed onto the polymer, and after 60 minutes 47% has been adsorbed.

EXAMPLE 2

200 mg of a polymer prepared according to Example B (particle size from 250 to 500 μm) are shaken in 20 ml of a solution of 100 mg of α-amylase (130 units/mg) in 0.005M sodium acetate buffer of pH 6.0 at 4° C. for 64 hours. The carrier is then washed at room temperature with 50 ml portions of 0.05M sodium acetate buffer of pH 6.0, twice for 5 minutes and twice for 1 hour. To determine the immobilized enzymatic activity, the carrier is shaken in 50 ml of a solution of 5 g of Zulkowsky starch (Merck) in 0.016M sodium acetate buffer of pH 6.0 at 30° C. for 30 minutes. The oligosaccharides formed are determined with 3,5-dinitrosalicylic acid in accordance with the method of P. Berenfeld (Methods in Enzymology, Volume I, 149, Academic Press, 1955). Activity of the carrier: 3.0 g of hydrolyzed starch per g and per hour.

EXAMPLE 3

200 mg of a polymer prepared according to Example C (particle size from 250 to 500 μm) are shaken in 20 ml of a solution of 100 mg of β-amylase (28 units/mg) in 0.05M sodium acetate buffer of pH 4.8 at 4° C. for 64 hours. The carrier is then washed at room temperature with 50 ml portions of 0.05M sodium acetate buffer of pH 4.8, twice for 5 minutes and twice for 1 hour. To determine the immobilized enzymatic activity, the carrier is shaken in 50 ml of a solution of 5 g of Zulkowsky starch (Merck) in 0.016M sodium acetate buffer of pH 4.8 at 30° C. for 30 minutes. The maltose formed is determined with 3,5-dinitrosalicylic acid in accordance with the method of P. Berenfeld (loc. cit.). Activity of the carrier: 2.3 g of maltose formed per g and per hour.

EXAMPLE 4

Amyloglucosidase is bonded to 200 mg of a polymer prepared according to Example B (particle size from 250 to 500 μm), by a method similar to that described in Example 2. The activity of the carrier is 15.3 g of glucose formed per g and per hour.

EXAMPLE 5

25 mg of a polymer prepared according to Example D are shaken with a solution of 250 mg of invertase (150 units/mg) at 4° C. for 64 hours. The polymer is then washed at room temperature with 100 ml portions of 0.0025M sodium acetate buffer of pH 5.3, twice for 5 minutes and once for 1 hour. The polymer is shaken in 50 ml of a solution of 17.5 g of sucrose in 0.001M of sodium acetate buffer of pH 5.3 for 10 minutes and the degree of hydrolysis is determined polarimetrically. Activity of the carrier: 275 g of sucrose per g and per hour. Amount of enzyme bonded: 2.4 mg per mg of polymer.

EXAMPLE 6

25 mg of a polymer prepared according to Example E are charged with invertase by a method similar to that in Example 5. Activity: 300 g of sucrose per g of polymer and per hour. Among of enzyme bonded: 1.3 mg per mg of polymer.

EXAMPLE 7

25 mg of a polymer prepared according to Example F are charged with invertase by a method similar to that in Example 5. Activity: 194 g of sucrose per g of polymer and per hour. Among of enzyme bonded: 1.5 mg per mg of polymer.

EXAMPLE 8

25 mg of a polymer obtained according to Example G are charged with invertase by a method similar to that in Example 5. Activity: 150 g of sucrose per g and per hour.

EXAMPLE 9

25 mg of a polymer obtained according to Example H are charged with invertase by a method similar to that in Example 5. Activity: 6 g of sucrose per g and per hour.

EXAMPLE 10

1 g of a polymer prepared according to Example C is charged with invertase by a method similar to that in Example 5. The polymer is then introduced into a column and is thermostatically controlled at 30° C. A solution of 640 g of sucrose/l (brought to pH 5.3) is pumped through the column at a rate of 100 ml/hour. Hydrolysis of the sucrose is monitored polarimetrically. After 1 day, the degree of hydrolysis is 92%, and after 20 days is 38%.

EXAMPLE 11

The carrier charged by method similar to that in Example 10 is treated, before being used, with 20 ml of a 0.1% strength solution of glutaraldehyde in water. The degree of hydrolysis obtained therewith is 95% after 1 day and 85% after 20 days.

We claim:

1. A water-insoluble protein material consisting essentially of a biologically active protein on a water-insoluble carrier, wherein the protein is adsorbed onto a water-insoluble copolymer based on 30 to 99 percent, by weight of the copolymer, of N-vinylimidazole or substituted N-vinylimidazoles, 1 to 70 percent by weight of a copolymerizable, polyolefinically unsaturated monomer and 0 to 69 percent by weight of monomers which are copolymerizable therewith.

2. The protein material of claim 1, wherein the copolymer is a bead polymer.

3. The protein material of claim 1 or 2, wherein the carrier contains, as the copolymerizable monomer, a polyolefinically unsaturated component.

4. The protein material of claim 3, wherein the polyunsaturated component of the carrier is divinylstyrene, a polyfunctional ester of acrylic acid or methacrylic acid, a polyolefinically unsaturated urea derivative or a polyolefinically unsaturated acid amide.

5. The protein material of claim 4, wherein the carrier contains, as a further comonomer, styrene, a ($C_{1-4}$-alkyl)-styrene, acrylic acid or methacrylic acid or an alkyl or aminoalkyl ester thereof or a vinylheterocyclic compound.

* * * * *